(12) United States Patent
Zhang et al.

(10) Patent No.: US 9,792,804 B2
(45) Date of Patent: Oct. 17, 2017

(54) SYSTEM AND METHOD OF MONITORING AN ELECTRONIC DISCHARGE DEVICE IN AN AIR PURIFICATION SYSTEM

(71) Applicant: Steril-Aire, Inc., Burbank, CA (US)

(72) Inventors: Kanghong Zhang, Burbank, CA (US); Robert M. Culbert, Manhattan Beach, CA (US); Robert Scheir, Sherman Oaks, CA (US); Richard Mueller, Burbank, CA (US)

(73) Assignee: Steril-Aire, Inc., Burbank, CA (US)

( * ) Notice: Subject to any disclaimer, the term of this patent is extended or adjusted under 35 U.S.C. 154(b) by 0 days.

(21) Appl. No.: 15/452,142

(22) Filed: Mar. 7, 2017

(65) Prior Publication Data

US 2017/0243460 A1 Aug. 24, 2017

Related U.S. Application Data

(63) Continuation of application No. 13/831,242, filed on Mar. 14, 2013, now Pat. No. 9,588,188, which is a continuation-in-part of application No. 12/580,581, filed on Oct. 16, 2009, now abandoned.

(60) Provisional application No. 61/106,366, filed on Oct. 17, 2008.

(51) Int. Cl.
| | |
|---|---|
| *G08B 5/00* | (2006.01) |
| *G08B 21/18* | (2006.01) |
| *G01R 31/44* | (2006.01) |
| *G01R 31/24* | (2006.01) |
| *G08B 5/36* | (2006.01) |

(52) U.S. Cl.
CPC .......... *G08B 21/18* (2013.01); *G01R 31/245* (2013.01); *G01R 31/44* (2013.01); *G08B 5/36* (2013.01)

(58) Field of Classification Search
CPC ........ G08B 21/18; G08B 5/36; G01R 32/245; G10R 31/44
USPC ............ 340/691.1; 95/52, 65, 149, 214, 234
See application file for complete search history.

(56) References Cited

U.S. PATENT DOCUMENTS

| | | | | |
|---|---|---|---|---|
| 4,757,422 A | * | 7/1988 | Bossard | H01T 23/00 361/231 |
| 5,475,364 A | * | 12/1995 | Kenet | G08B 19/005 340/522 |
| 6,125,638 A | * | 10/2000 | Ji | C03B 37/02718 62/322 |

(Continued)

*Primary Examiner* — Ojiako Nwugo
(74) *Attorney, Agent, or Firm* — Edell, Shapiro & Finnan, LLC

(57) ABSTRACT

A method and system of remotely monitoring an operational status of electronic discharge devices in an air purification system senses emitted radiation at a location proximate the air purification system, alone or in combination with a determination of an amount of time remaining in an operational lifetime of the electronic discharge device, or an amount of power delivered to at least one of the electronic discharge devices. A determination of the operational status of at least one of the electronic discharge devices is made based on at least emitted radiation, and the status information is transmitted to a remote monitoring unit that receives the status information and displays an indicator of operational status. In one embodiment, the operational status of a UV-C germicidal lamp may be monitored using optically sensitive devices located within a purification system.

10 Claims, 13 Drawing Sheets

(56) References Cited

U.S. PATENT DOCUMENTS

| | | | | |
|---|---|---|---|---|
| 2001/0007091 A1* | 7/2001 | Walter | ............. | G06F 11/006 |
| | | | | 702/107 |
| 2003/0039299 A1* | 2/2003 | Horovitz | ............. | G01N 27/123 |
| | | | | 374/141 |
| 2003/0056648 A1* | 3/2003 | Fornai | ............. | B01D 47/06 |
| | | | | 95/65 |
| 2006/0035122 A1* | 2/2006 | Weissman | ............. | B01D 53/22 |
| | | | | 429/423 |
| 2008/0196702 A1* | 8/2008 | Fukagai | ............. | F02D 41/1456 |
| | | | | 123/688 |
| 2009/0185959 A1* | 7/2009 | Weber | ............. | C01B 13/11 |
| | | | | 422/107 |

* cited by examiner

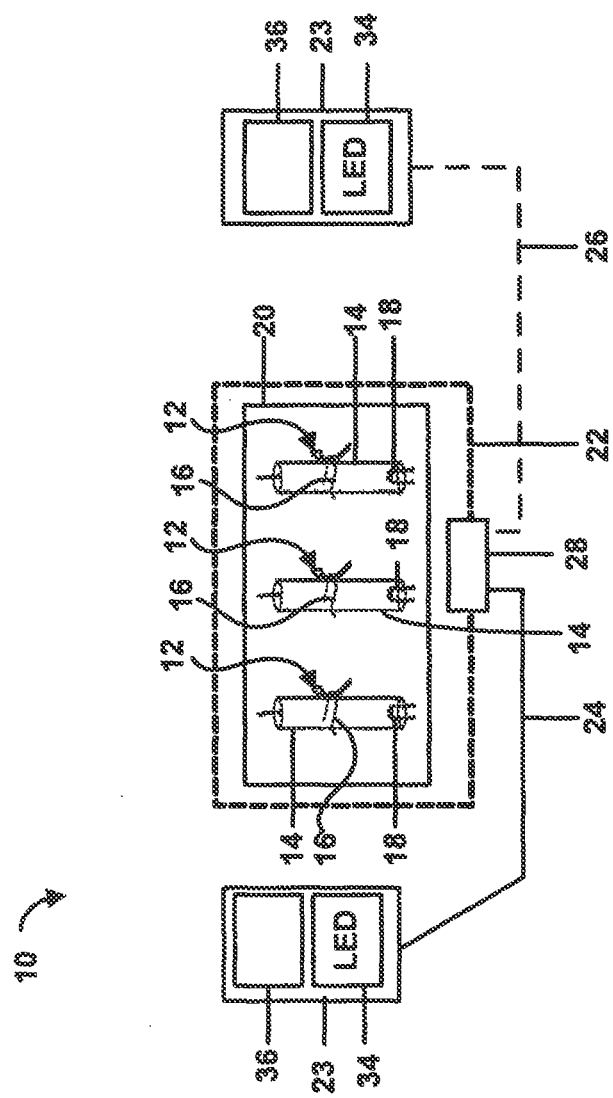

SYSTEM AND METHOD OF MONITORING AN ELECTRONIC DISCHARGE DEVICE IN AN AIR PURIFICATION SYSTEM

CROSS REFERENCE TO RELATED APPLICATION

This application is a Continuation of application Ser. No. 13/831,242, filed Mar. 14, 2013, which is a Continuation-in-Part of application Ser. No. 12/580,581, filed Oct. 16, 2009, which claimed priority to U.S. Provisional Application Ser. No. 61/106,366, filed Oct. 17, 2008, the contents of which are incorporated by reference herein in their entirety.

BACKGROUND OF THE INVENTION

I. Field of the Invention

The present invention relates generally to air purification systems, More particularly, the present invention relates to a system and method of monitoring air purification systems that utilize one or more electronic discharge devices.

II. Discussion of the Related Art

Air purification systems may be used to address growing concerns over pollution, air-born biological materials, allergens, and the need to provide a clean environment for the production of advanced electronic materials, Such air purification systems sometimes use an electronic discharge device (EDD) installed in heating, ventilation, and air conditioning (HVAC) systems. The electronic discharge device provides germicidal treatment using ultra-violet (UV) radiation to eradicate harmful microorganisms in the air and on surfaces of an air handling unit of the air purification system. Optimum performance of an air purification system depends on the electronic discharge devices operating at peak efficiency.

Electronic discharge devices commonly used in air purification systems have a finite lifetime and must be replaced periodically. In current systems, a device may malfunction, unknown to a maintenance provider, resulting in a significant delay in replacing the device. Degradation in performance due to the device malfunctioning may substantially reduce purification capabilities of the system.

Some air purification systems are provided with status indicators, for example, a status indicator window or a light-emitting diode (LED). Some air purification systems are mounted on air handling units with limited physical access making it difficult to view the status indicator window or LED. It may also be difficult to monitor an operational status of a particular electronic discharge device when the status indicator is provided at a location proximate the purification system.

Additionally, typical electronic discharge device status indicators use electrical properties such as voltage, current, and resistance sensed at various locations within the device to determine an operational status of an electronic discharge device. Such configurations are ill suited for retrofitting and may not be able to provide a comprehensive description of a status of an electronic discharge device.

SUMMARY OF THE INVENTION

It is therefore a primary object of the present invention to overcome disadvantages of the prior art by providing an improved system and method of monitoring an operational status of an electronic discharge device in an air purification system. The system and method may be provided by an original equipment manufacturer (OEM) or as a retrofit to an existing air purification system.

The present invention achieves this object by providing a system of monitoring an operational status of an electronic discharge device in an air purification system that includes a sensor located proximate an air purifying system and configured to detect an operational characteristic of an electronic discharge device in an purification system and a sensing circuit located proximate the air purification system and configured to receive input signals from the sensor, determine an operational status of the electronic discharge device in response to the operational characteristic detected, and transmit a signal indicating the operational status of the electronic discharge device to a remote location. In an embodiment, the sensor includes a photodiode that is sensitive to ultra-violet radiation.

In an embodiment, the sensor includes a mounting device configured to mount the sensor to an electronic discharge device. In another embodiment, the sensor includes a masking element formed of opaque material configured to prevent cross-illumination from any adjacent electronic discharge devices. In an embodiment, the system may include a monitoring unit configured to receive the signal from the sensing circuit and display an indicator of the operational status of the electronic discharge device.

In another embodiment, a system of monitoring an operational status of an electronic discharge device in an air purification system includes an optically sensitive detector configured to detect radiation emitted from an electronic discharge device and located within an purification system and in an optical path of radiation emitted from the electronic discharge device, wherein the detector is configured to generate a signal in response to a level of radiation detected and a sensing circuit configured to receive input signals from the optically sensitive detector and determine an operational status of the electronic discharge device in response to the optical radiation detected. In an embodiment, the system may include a monitoring unit configured to receive a signal from the sensing circuit and display an indication of the operational status of the electronic discharge device.

The present invention also relates to a method of remotely monitoring an operational status of an electronic discharge device in an air purification system that comprises sensing an operational characteristic of an electronic discharge device of an air purification system, determining an operational status of the electronic discharge device in response to the operational characteristic sensed, and transmitting a signal indicating the operational status of the electronic discharge device to a remote location.

In an embodiment, the electronic discharge device includes an ultra-violet (UV) lamp configured to emit germicidal UV-C radiation. In another embodiment, the operational characteristic sensed includes emitted radiation, alone or in combination with an amount of operational lifetime remaining for the electronic discharge device, and/or an amount of power delivered to the electronic discharge device. In an embodiment, light-emitting diodes (LED) display any one of sensor information, operational lifetime information, and electronic discharge device power information.

In an embodiment, a method of remotely monitoring an operational status of an electronic discharge device in an air purification system includes sensing optical radiation emitted from an electronic discharge device using an optically sensitive detector located within an purification system and in an optical path of the radiation emitted from the electronic discharge device, generating a signal in response to the optical radiation sensed, determining an operational status of the electronic discharge device using the signal generated by the optically sensitive detector, and transmitting a signal indicating the operational status of the electronic discharge device to a remote location. In an embodiment, the method may also include receiving the signal at the remote location and displaying an indication of the operational status of the electronic discharge device at the remote location.

In another embodiment a method for monitoring the operational status of a plurality of electronic discharge devices in an air purification includes sensing an operational characteristic of the plurality of electronic discharge devices, determining an operational status of the plurality of electronic discharge devices based on the sensing, and indicating the operational status of the plurality of electronic discharge devices based on the determining. In an embodiment, the electronic discharge devices are grouped into first and second groups of devices, and the operational characteristic is a difference between one or more electrical properties of the first and second groups of devices. This characteristic may be, for instance, a difference in the relative current of the first and second groups of devices.

In another embodiment, an apparatus for remotely monitoring an operational status of a plurality of electronic discharge devices in an air purification system includes a sensing stage that has at least one adjustable impedance element and is configured to measure a first electrical property of a first array of electronic discharge devices and a second electrical property of a second array of electronic discharge devices. The electrical property may be, for instance, current and the sensing stage may include one or more current sensing loops. The apparatus also includes an imbalance detection stage configured to generate an operational status signal and an indicator that is configured to provide an indication of the operational status based at least in part on the operational status signal, In an embodiment, the operational status signal is indicative of whether a difference between the first and second electrical properties has exceeded a predetermined threshold.

In yet another embodiment, a method of retrofitting an existing air purification system for monitoring an operational status of an electronic discharge device in an air purification system including accessing an existing air purification system comprising an electronic discharge device located within an air handling unit wherein the electronic discharge device is configured to expose air moving through the unit to radiation and installing within the purification system and in an optical path of the radiation emitted from the electronic discharge device an optically sensitive device to detect radiation emitted from the electronic discharge device.

In another embodiment a method of retrofitting an air purification system, which has a plurality of electronic discharge devices, includes installing a first current sensing loop to a first array of devices and a second current sensing loop to a second array of devices. In an embodiment, the method also includes performing a balance adjustment on a sensing circuit connected to the current sensing loops, and optionally, a balance readjustment. The adjustment and readjustment can include modifying an adjustable component of the sensing circuit such that the sensing circuit indicates that one or more electrical properties of the first and second arrays are balanced.

Some of the advantages of the present invention are that a facilities manager or other individual may monitor an operational status of an air purification system from a location that is physically remote from the air purification system, such as from an office or central panel, reducing a delay in replacing or servicing malfunctioning electronic discharge devices, reducing an amount of time an air purification system operates at a reduced level of efficiency, and existing air purification systems may be retrofitted with remote monitoring to provide for these advantages.

Other objects and advantages of the present invention will become apparent to those of skill in the art upon reviewing the detailed description of the preferred embodiments and accompanying drawings.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers indicate identical or functionally similar elements.

FIG. 3 is a diagram showing a remote monitoring system for an air purification system in an air handling unit according to an embodiment of the present invention.

DESCRIPTION OF THE PREFERRED EMBODIMENTS

Figure 1:
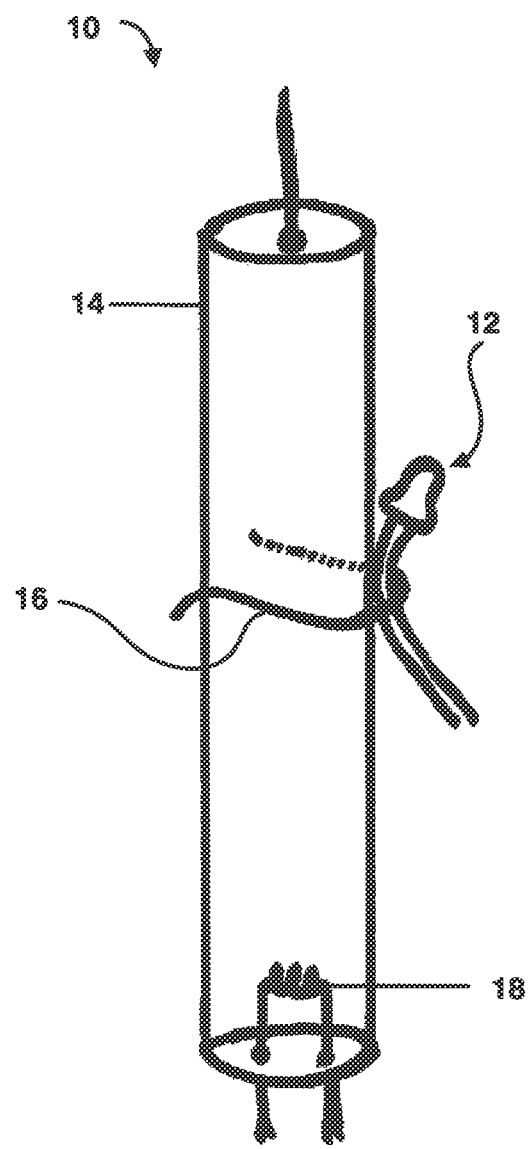
FIG. 1 is a diagram showing part of an electronic discharge device monitoring system for use with an air purification system according to an embodiment of the present invention.

FIG. 1 shows an embodiment of an electronic discharge device (EDD) monitoring system 10 for an air purification system according to the present invention. The system 10 includes a sensor 12 mounted in relation to an EDD 14 of an air purification system to monitor an operational characteristic of the EDD. The term "operational characteristic," as used herein, refers to a physical property of the EDD that relates to operational status or performance such as, for example, an amount of radiation emitted by the EDD. In accordance with the present invention, the sensor 12 detects an operational characteristic of the EDD and generates a signal indicative of the operational status of the EDD.

In a preferred embodiment, the sensor 1 is an optical detector, such as a photodiode or a photoresistor, operable to detect the amount of germicidal radiation emitted from the EDD 14. The electronic discharge device 14 may be a fluorescent, mercury vapor, ultraviolet (UV), low pressure sodium, high pressure or other lamp made of glass, metal, plastic or other material to provide radiation to eradicate harmful microorganisms in the air and on surfaces of an air handling unit, In a preferred embodiment, the sensor 12 is mounted in relation to an EDD 14 in the form of an ultra-violet (UV) lamp configured to emit germicidal UV-C radiation with a wavelength of approximately 250-260 rim, The UV lamps 14 may be, for example, of the single or double ended variety and have a straight, J-shaped, or U-shaped tube, The sensor 12 is preferably attached directly to the EDD 14, in the path of emitted radiation, using a mounting mechanism 16. According to an embodiment, the mounting mechanism 16 is a resilient clip that detachably mounts the sensor 12 to an external surface of the EDD 14. In the embodiment shown, the mounting mechanism 16 is a semi-circular clip without-turned ends. The clip 16 is preferably formed of a heat resistant, elastic material, such as stainless steel, and has a radius of curvature slightly smaller than a radius of curvature of the lamp 14 so that, when installed around the lamp as shown, the clip is elastically deformed outward and caused to exert an inwardly directed mounting pressure against the lamp. The out-turned ends of the clip 16 facilitate installation and removal of the clip without the need of tools.

According to an embodiment, the sensor 12 is mounted at a central location along a longitudinal axis of the EDD 14, preferably at least several inches from the filament 18. This location maximizes exposure to emitted radiation while reducing heating of the sensor 12 by the filament 18 that can potentially interfere with performance and reliability of the system. It is to be understood that the sensor 12 may be used either alone or in combination with other sensors to monitor operational status of the air purification system. For example, the sensor 12 may be used with other status indicators such as, for example, operational life and purification system power indicators.

Figure 2A:
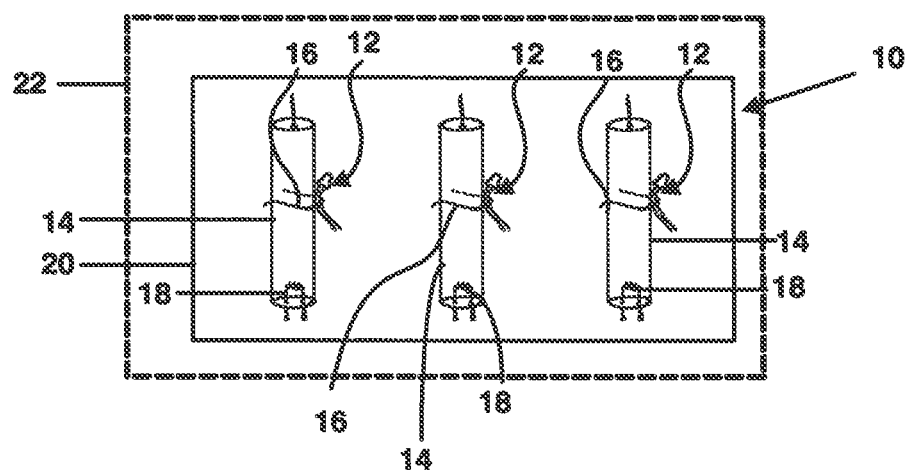
FIG. 2A is a diagram showing an embodiment of the monitoring system in conjunction with an air purification system utilizing a plurality of electronic discharge devices disposed within an air handling unit.

FIG. 2A shows an embodiment of the monitoring system 10 configured for use with an air purification system 20 that includes a plurality of electronic discharge devices 14 located within an air handling unit 22, such as an HVAC system (e.g., like the air purification systems shown and described in U.S. Pat. Nos. 5,334,347 and 5,817,276, the disclosures of which are incorporated herein by reference). The monitoring system 10 includes a plurality of sensors 12 mounted on a plurality of EDDs 14 using a plurality of mounting mechanisms 16 to monitor an operational characteristic of each EDD, The plurality of optically sensitive sensors 12 may be installed within the air purification system 20 to monitor an amount of radiation emitted by the electronic discharge devices 14. The sensors 12 are preferably located near the electronic discharge device 14 and in an optical path of emitted radiation such that the sensor 12 may detect radiation emitted under normal operating conditions. Preferably, the sensors 12 are mounted at a central location along a longitudinal axis of the EDD and are of a size that does not interfere with the germicidal treatment process by blocking radiation.

Figure 2B:
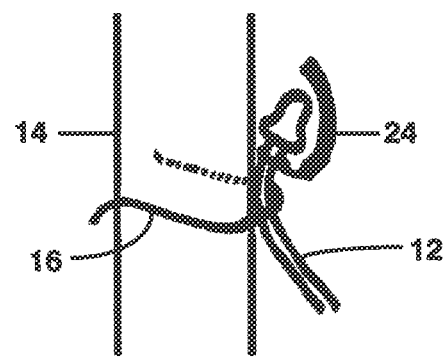
FIG. 2B is an enlarged view of a monitoring system sensor mounted on an electronic discharge device with a shield according to an embodiment of the present invention.

According to an embodiment, shown in FIG. 2B, a shield 24 may be provided on each sensor 12 to reduce cross-illumination from adjacent electronic discharge devices 14. The shield 24 enables the sensors 12 to detect a more accurate amount of radiation being emitted from the electronic discharge device 14 to which the sensor 12 is mounted, According to an embodiment, the shield 24 may be, for example, a masking element disposed between the sensor 12 and an adjacent electronic discharge device 14 and formed of material opaque to ultra-violet C (UVC) radiation. The shield 24 is shown as a curved element that extends around a side of the sensor 12 opposite the EDD 14, although other shield configurations may be used. The shield 24 may also be configured to be manually detachable from the sensor 12 such that the shield may be reattached or attached to a replacement sensor 12, if desired.

It will be appreciated that the sensors 12 provide a reliable measure of actual performance of an electronic discharge device 14 by detecting the presence of germicidal radiation in the air purification system 20. The sensors 12 are configured to generate a signal, such as a voltage or current signal, in response to a level of radiation detected, thereby giving an indication of the performance of the electronic discharge device 14.

Referring to FIG. 3, it can be seen that the signals generated by the sensors 12 may be received by a sensing circuit 28 that transmits a status signal to a remote monitoring unit 23, The remote monitoring unit 23 may be positioned at a location that is not proximate the air handling unit 22, thereby allowing an individual such as a facilities engineer or other individual to monitor the status of one or more electronic discharge devices 14 within an air purification system 20 without needing to be in visual range of the system. In accordance with an embodiment of the present invention, the remote monitoring unit 23 may be configured with a passive reception device 36 that receives a status signal from the sensing circuit 28. Use of passive electronics at the back end reduces cost, thus providing a cost effective and easily implemented method of monitoring the status of electronic discharge devices within an air purification system from multiple locations. Additionally, the use of passive devices reduces a likelihood of interference among devices when multiple monitoring systems 10 are being used. It will be appreciated that the sensor circuit 28 may send a status signal to the remote monitoring unit 23 over a wired connection 24 or a wireless connection 26.

The remote monitoring unit 28 is configured to provide a sensible indication of the operational status of the electronic discharge devices 14. In a preferred embodiment, the indicator may be a visible indicator such as a light emitting diode (LED) 34 that shows a predetermined color corresponding to a detected operational status of the EDDs. If desired, a plurality of indicators corresponding to the number of EDDs may be used so that a user may determine which of the EDDs is malfunctioning and in need of replacement. The indicator 34 on the remote monitoring unit 23 may also display, or be combined with other indicators that display, other operational characteristics such as operational lifetime information, and electronic discharge device power information.

Figure 4:
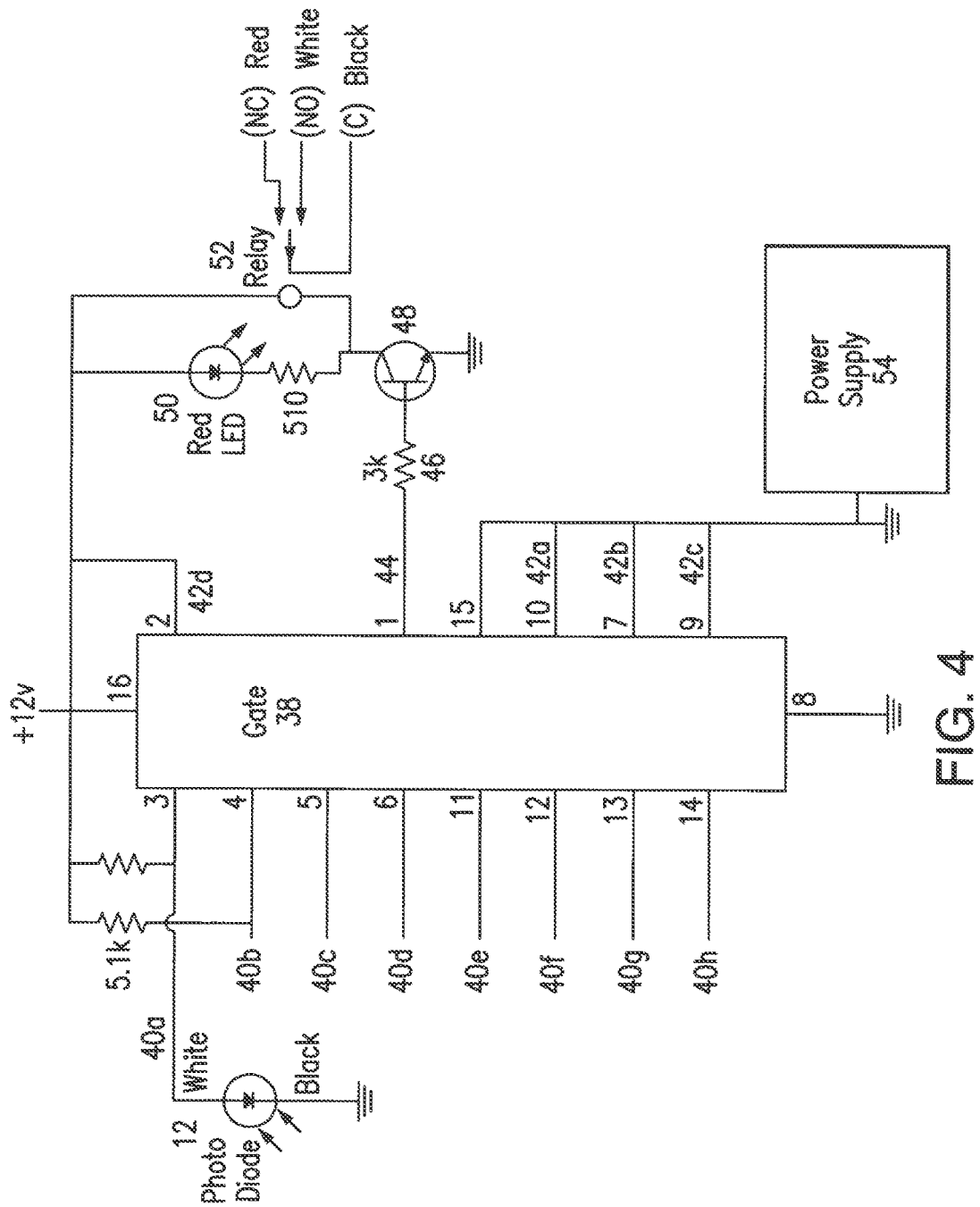
FIG. 4 is a sensing circuit for an electronic discharge device monitoring system according to an embodiment of the present invention.

FIG. 4 shows an embodiment of a sensing circuit 28 according to the present invention. The sensing circuit 28 may include a multifunction gate 38 having inputs 40a-40h. The sensing circuit 28 is configured to receive input signals from the sensors 12 using one or more of the inputs 40a-40h. If there are fewer than eight (8) inputs, a dual in-line package (DIP) switch may be used to configure the multifunction gate 38. The multifunction gate 38 may include one or more binary control inputs 42a-42c to control the implementation of different logic functions. In an embodiment, binary control input 42d may be used to control whether output 44 is set as a logic "1" or a logic "0" in response to inputs 40a-40h and the inner states of the multifunction gate 38.

The sensing circuit 28 is configured to determine an operational status of the electronic discharge devices 14 in response to the signal received from sensors 12 using inputs 40a-40h. An output signal that indicates the state of the multifunction gate 38 is communicated using the output 44. In an embodiment, the multifunction gate 38 may be configured as an AND gate. In this configuration, the multifunction gate 38 sets output 44 as logic "1" if all inputs 40a-40h receive a signal from sensors 12 above a given threshold. The level of the signal delivered from sensors 12 is dependent on the sensed intensity of radiation from the electronic discharge devices 14. If not all sensors 12 receive a signal above the given threshold, the output 44 will be a logic "0". Thus, a determination of operational status may be made on the basis output 44. The operational status may refer to how well the electronic discharge device 14 is performing. For example, an operational status may be "fully operational", "reduced capacity", "malfunction" or other status.

The output 44 is connected to a sensing resistor 46 and a switch 48. The switch 48 is controlled by the output 44, and may be in the "ON" or "OFF" position depending on whether output 44 is a logic "1" or logic "0". The switch 48 may be connected to a light-emitting diode (LED) 50 such that the LED 50 may be used to provide a visual indication regarding the operational status of the electronic discharge device 14. For example, a red LED 50 may be used to indicate a malfunction status of the electronic discharge device 14 depending upon the state of output 44. The sensing circuit 52 may also include a relay 52 that may be connected to one or more LEDs 50 to provide additional operational status indications to a remote monitoring unit at a remote location.

The sensing circuit 28 may also include a commercially available power supply 54 and a timer that indicates an operational lifetime remaining for the electronic discharge device 14. The timer may be used hi conjunction with the LED 50 to indicate the operational lifetime remaining.

Figure 5:
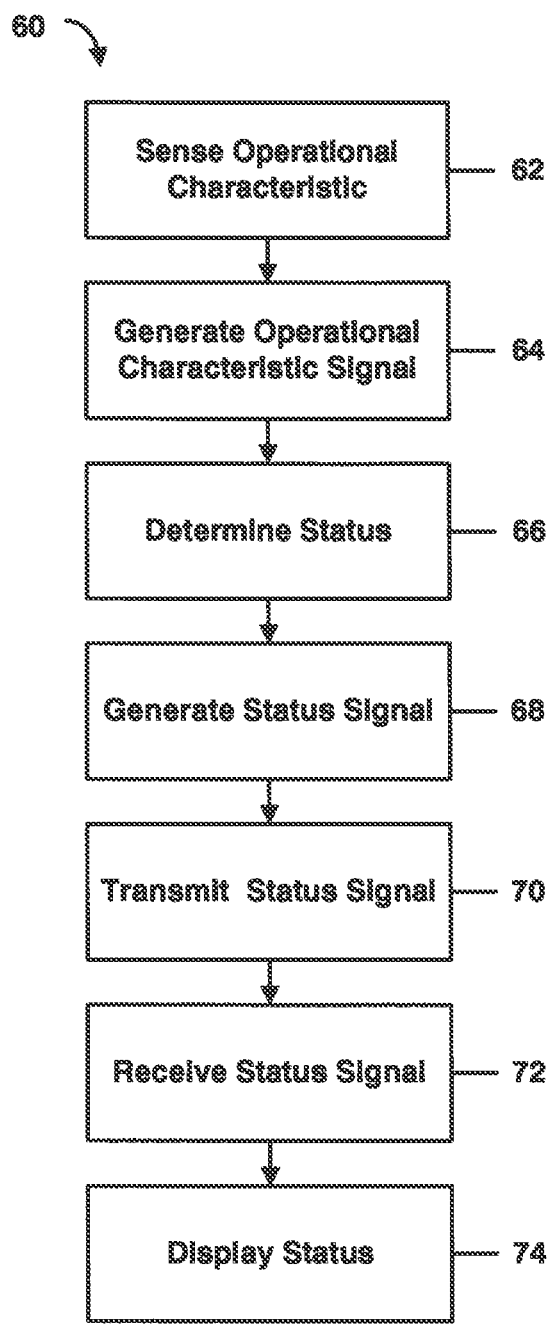
FIG. 5 is a flowchart of a method of monitoring an electronic discharge device in an air purification system according to an embodiment of the present invention.

FIG. 5 shows a method 60 of remotely monitoring an electronic discharge device in an air purification system according to an embodiment of the invention. The method 60 may begin at step 62 where a sensor senses an operational characteristic of the electronic discharge device. As discussed above, the sensor may be, for example, an optically sensitive detector and the optical characteristic may be, for example, an amount of radiation emitted from an electronic discharge device, an amount of operational lifetime remaining for an electronic discharge device, whether the electronic discharge device is receiving power or other characteristic.

An operational characteristic signal may be generated in step 64 that is indicative of the operational characteristic sensed in step 62. Using the operational characteristic signal, a status of the electronic discharge device may be determined in step 66. The status may be, for example, "fully operational", "reduced capacity", "malfunction" or other status.

A status signal indicating the status of the electronic discharge device may be generated in step 68. The status signal may be transmitted, in step 70, to a monitoring unit such as, for example, a control panel. According to an embodiment, the monitoring unit may be in a remote location. The status signal may be received by the monitoring unit in step 72. A status of the electronic discharge device, based on the status signal received, may be displayed in step 74 using any display device.

According to some embodiments, the operational status of an EDD may be assessed by sensing a change in an electrical property, such as current flow, of one or more EDDs relative to other EDDs. In certain aspects, a method of remotely monitoring an operational status of an electronic discharge device includes sensing an imbalance in the current levels of two or more lamp arrays, each including at least one EDD. For instance, sensing an operational characteristic, such as in step 62 of method 60, may include sensing an imbalance between the current of a first lamp array and second lamp array. The current of each loop may be measured, for instance, using a current sensing loop. Accordingly, an operational characteristic signal, such as the signal generated in step 64 of FIG. 5, may be generated based on a change in the relative current flow of two or more lamp arrays. The relative current flow of the lamp arrays may indicate that the EDDs of the lamp arrays are fully operational, for instance, if the current flow is balanced. Alternatively, the relative current flow may indicate that one or more EDD is operating at reduced capacity or has malfunctioned, for instance, if the current flow between the lamp arrays is imbalanced.

Figure 6:
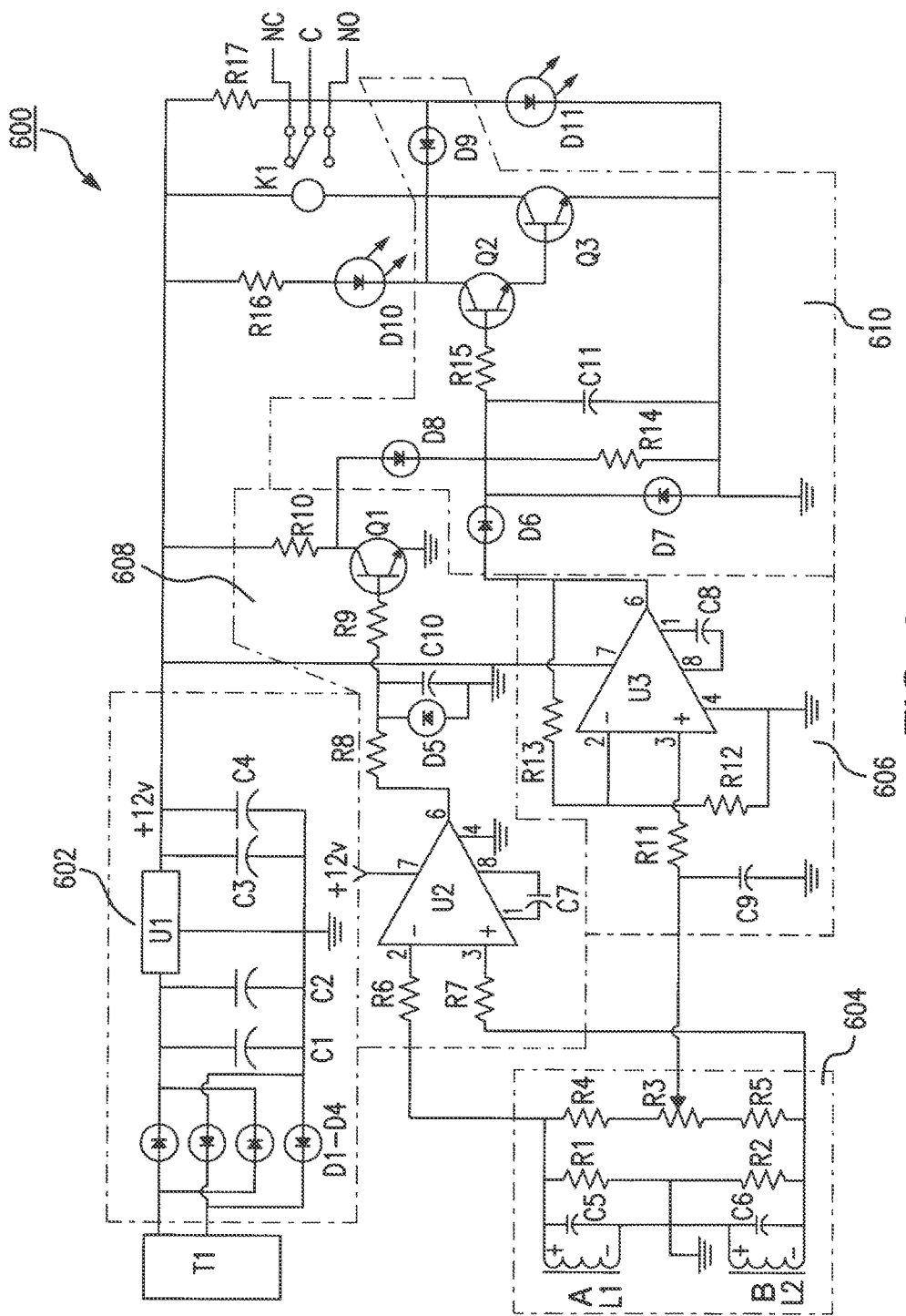
FIG. 6 is a sensing circuit for an electronic discharge device monitoring system according to embodiments of the present invention.

Referring now to FIG. 6, a schematic illustration of a sensing circuit 600 for an electronic discharge device monitoring system according to some embodiments is provided. The sensing circuit 600 may be used, for instance, to implement one or more steps of method 60 shown in FIG. 5.

Power may be supplied to sensing circuit 600 using a transformer T1, such as an external wall transformer. Transformer T1 may be used to step down AC voltage, for instance, to produce a 20 v AC output based on either a 120 v or 240 v input. In some embodiments, transformer T1 may be separate from the remaining elements of circuit 600 and connected via a socket, through an opening in an enclosure of the circuitry housing, or by a standardized miniature AC/DC plug. The voltage for circuit 600 may be regulated by a voltage regulator stage 602 comprised of a plurality of diodes and capacitors, such as diodes D1-D4, capacitors C1-C4, and voltage regulator U1 as shown in FIG. 6. This stage can provide a voltage, for example +12 v, and a return (ground) to the remaining components of circuit 600.

According to certain aspects, some or all of the EDDs used in an air purification system can be grouped into first ("A') and second ('B") lamp arrays. The example shown in FIG. 6 and described herein is illustrated using two lamp arrays; however, this description is only an example and one of ordinary skill in the art will recognize that the techniques and structure of the present invention can be extended to three or more groups of law arrays. The current of each array may be sensed by a current loop, for instance, as part of sensing stage 604. For example, the current of array A may be sensed by a first current loop, illustrated as L1 FIG. 6, while the current of array B is sensed by a second current loop, L2. According to some embodiments, the lamp arrays are equally loaded, e.g., contain the same number of EDDs and/or draw the same amount of current under normal operating conditions.

In the example circuit 600, any preliminary loading and filtering required by current loops L1 and 12 may be accomplished using capacitors CS, C6 and resistors R1,R2. The current loops Li and 12 may also be connected to a voltage divider comprising resistors R3-R5. According to some embodiments, one or more of the resistors in the voltage divider of sensing stage 604 can be adjustable, such as, for example, balance resistor R3 of circuit 600. The balance resistor may be adjusted such that, when all the EDDs of the first and second arrays (A,B) are illuminated and stable, the electrical properties of the two arrays appears to be equivalent. In other words, resistor R3 can be adjusted such that no imbalance is presented to detection stage 606 of circuit 600 under normal operating conditions.

According to some embodiments, the sensing circuit 600 may include one or more LEDs or status lamps to help indicate whether there is an imbalance between the first and second lamp arrays. The LEDs may be, for example, red and green. In certain aspects, circuit 600 includes a power detection stage 608 that insures that a first lamp D10, for instance a red blinking LED, will be illuminated if there is no power to the EDDs, The power detection stage 608 is comprised of an amplifier U2, and resistors R6-R10, capacitors C7 and C10, diode D5, and transistor 01. These components insure that a lamp, such as red LED/status lamp D10 is illuminated (e.g., blinking) if there is no power to the lamp arrays. Current through LED D10 is limited by resistor R16.

Imbalance detection stage 606 may be configured to detect an imbalance between the lamp arrays A and B. The stage may include, for example, an amplifier U2 and a number of additional components, such as resistors R11-R13 and capacitors C8 and C9. In some embodiments, the outputs of imbalance stage 606 and power detection stage 608 are connected to a summing stage 610. In the example of FIG. 6, diodes D6-D8 effectively add the signals from U2 and U3, which are applied to relay K1 and LED/status lamp drives Q2 and Q3. Accordingly, in certain aspects, red indicator light D10 can be either blinking or extinguished depending on the outputs of U2 and U3. Similarly, green indicator light D11 can be either illuminated or extinguished depending on the outputs of U2 and U3. The current through D11 can be limited by a resistor, such as R17 in the example of FIG. 6. The summing stage 610 in the example of FIG. 6 is supported by resistors R14 and R15, diode D9, as well as capacitor C11. In some embodiments, relay K1 supplies normally open and normally closed contacts for users to connect circuit 600 to existing alarm systems.

In some embodiments, one or more stages of sensing circuit 600 can be configured such that the imbalance must be greater than a predetermined threshold in order for the imbalance to be detected and/or indicated. For instance, a current differential of at least 10% may be required in order for an indication light to be illuminated or extinguished. Similarly, the threshold may be set between 5% and 10%. However, one of ordinary skill in the art will recognize that the threshold may be set according to the number of devices in the lamp arrays. For instance, a small threshold may be necessary in the circumstance where there are a large number of devices in each array.

Regarding another aspect of the present invention, the above referenced components, systems, and methods may be implemented in a pre-existing air purification system containing an electronic discharge device used to expose air moving though the unit to radiation specifically targeted to improve air quality. By accessing an existing the air purification system and installing an optically sensitive device sufficiently near the electronic discharge device to detect radiation emitted, for example, under normal operating conditions, the pre-existing air purification system may be configured for remote monitoring using the method described above.

According to some embodiments, a pre-existing air purification system containing multiple EDDs can be retrofitted to include an optical characteristic sensing circuit, such as sensing circuit 600 illustrated in FIG. 6. In certain aspects, a retrofitting kit may be provided to customer/user to install a sensing circuit. For example, a retrofitting kit may include a sensor box, which can include a sensing circuit such as circuit 600, multiple current sensing loops, a transformer, such as a 120 v AC to 20 v AC wall transformer, mounting equipment, and instructions for installation and/or operation.

Figure 7:
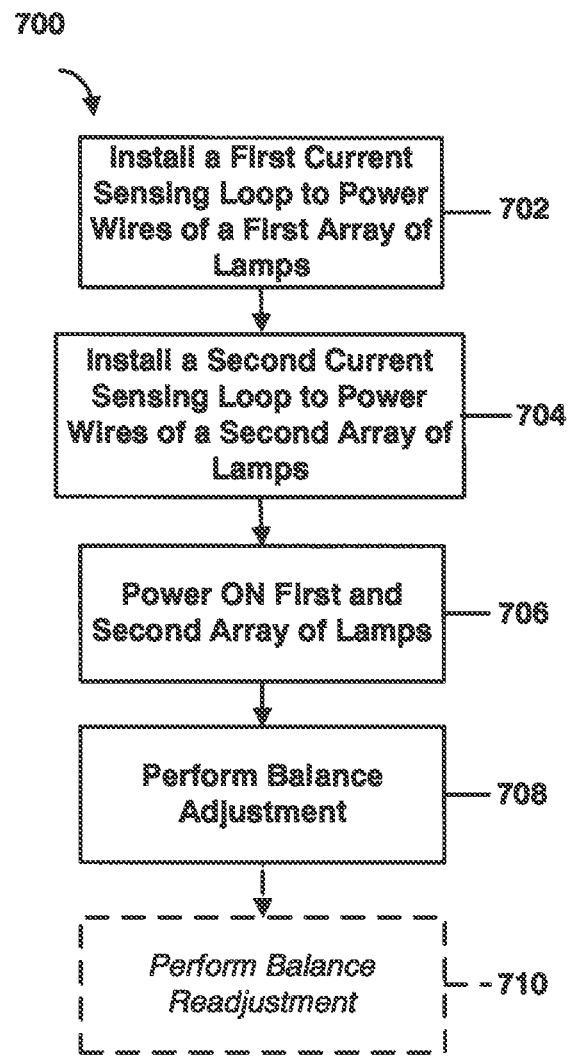
FIG. 7 is a flow chart of a method of retrofitting an air purification system.

Referring now to FIG. 7, a process 700 for retrofitting a pre-existing air purification system is provided. The system may be retrofitted to include electronics to sense an imbalance in the current levels of two or more lamp arrays, each including at least one EDD, According to some embodiments, the EDDs (e.g., UV lamps) of the system may be grouped into first and second lamp arrays, The grouping may be selected, for instance, such that the number of lamps in each array is the same. In certain embodiments, where there is an uneven number of total lamps, the grouping may be such that on array has 1 more lamp than the other, In step 702, a first current sensing loop is installed to the power wires of the first lamp array. This installation may include, for example, disconnecting a main power wire to the first lamp array and passing the wire through the first current sensing loop. The power wire may then be reconnected to the first lamp array.

In step 704, a second current sensing loop is installed to the power wires of the second lamp array. This installation may include, for example, disconnecting a main power wire to the second lamp array and passing the wire through the second current sensing loop. The power wire may then be reconnected to the second lamp array, According to some embodiments, the first and second current sensing loops are connected to a sensing circuit. The sensing circuit may be contained within housing or other packaging, such as a sensor box, The sensor box may be mounted, for instance, in a location as close as possible to the AC lines power the UV lamps to be monitored. Further, the sensor box may be mounted on the outside of a duct work component in a location that is protected moisture, such as rain. The sensor box may also be connected to one or more external monitoring or alarm systems. In certain aspects, information sensed by the sensing circuit may be communicated, for instance via a wired or wireless connection, to the external monitoring or alarm systems.

In step 706, the first and second lamp arrays should be powered ON. This step may include connecting an output of a transformer to the sensor box. According to some embodiments, an indicator, such as LED/status lamp D10 of circuit 600, can be illuminated (or blinking) to indicate that the sensor box is powered.

In step 708, a balance adjustment is performed. The balance adjustment may include, for example, adjusting an adjustable component of the sensing circuit. For instance, adjustable resistor R3 of circuit 600 can be adjusted to "balance" the first and second lamp arrays. In some embodiments, performing a balance adjustment 708 can include identifying a balancing "window." The adjustable component can be modified in a first direction to a first position, for instance, by using a screwdriver to turn an adjustment screw of an adjustable component, until a first indicator is illuminated. The first indicator may be, for example, green LED D11 of circuit 600, The adjustable component may then be further modified (e.g., rotated) to a second position where the first indicator changes, for instance, until the green LED is extinguished, and a second indicator, such as the red LED, is illuminated. Thus, the first and second position define a "window" where the first indicator shows that the two arrays of lamps are balanced. In certain aspects, the adjustable component may be set at a mid-point of the window.

Optionally, the process 700 may include a step 710 where the system is readjusted. For instance, this may include repeating step 708, defining a new window, and resetting the adjustable component to its mid-point.

Figure 8A:
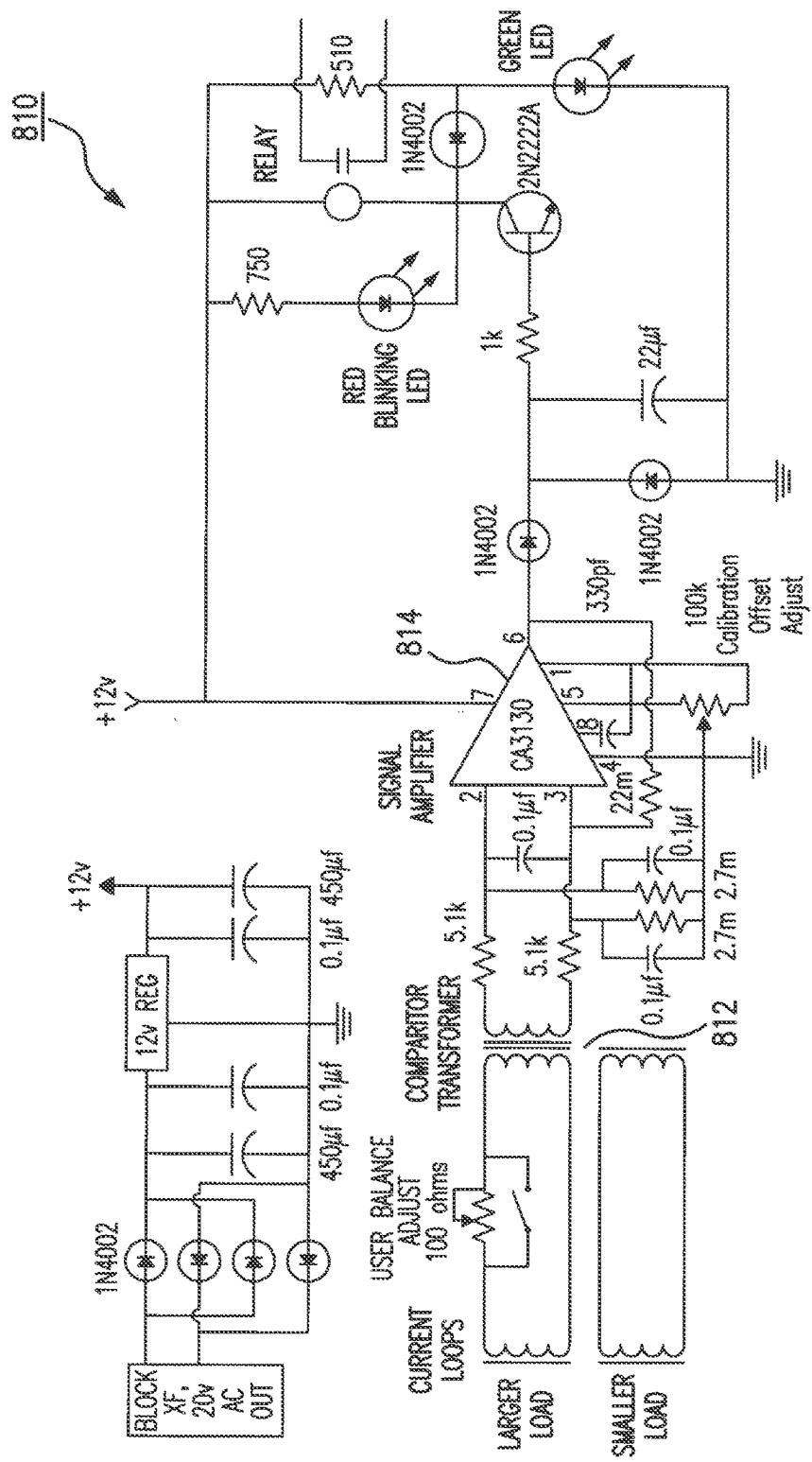
FIGS. 8A-8E are sensing circuits for an electronic discharge device monitoring system according to embodiments of the present invention.
Figure 8B:
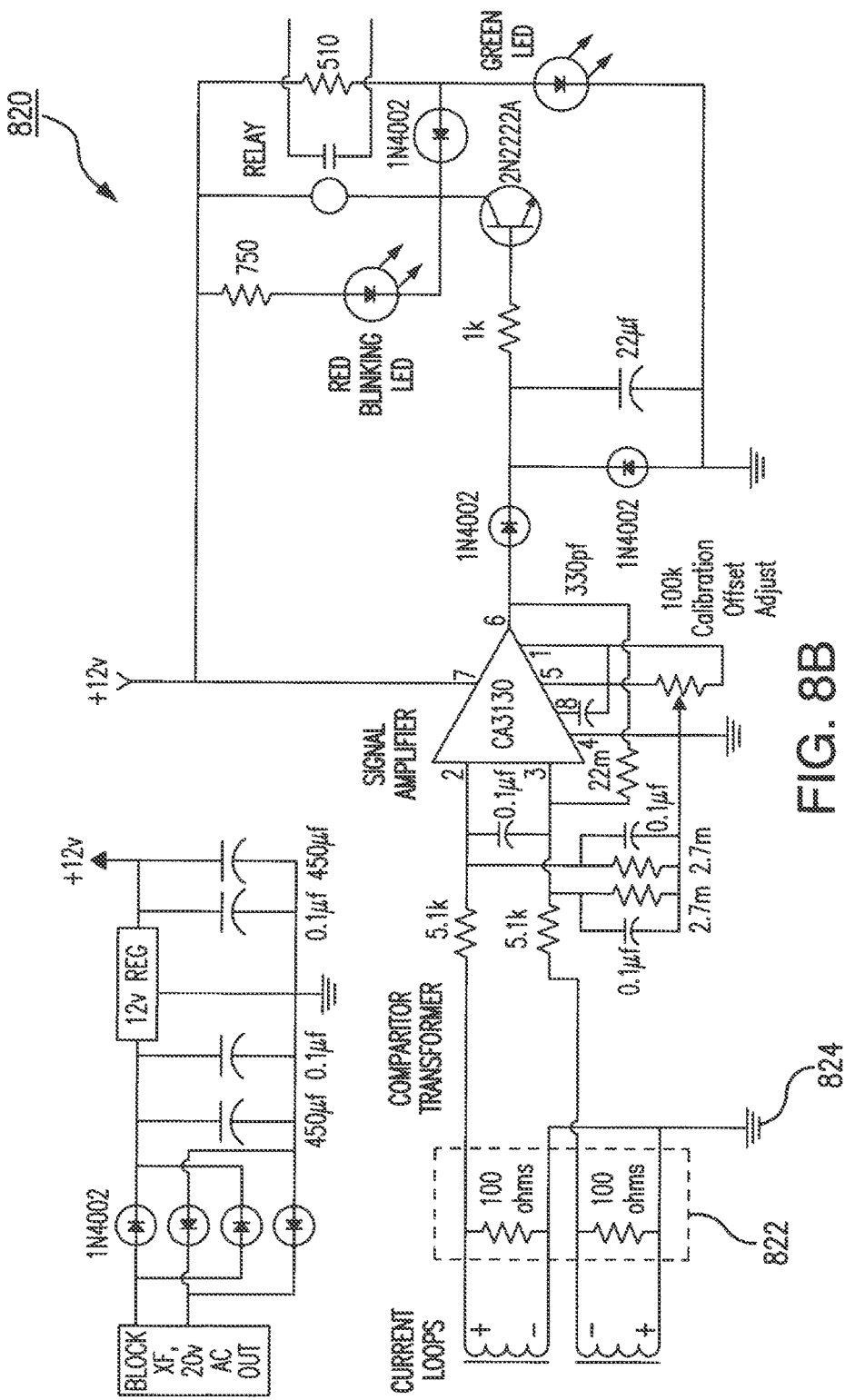

Referring now to FIGS. 8A-8E, additional exemplary sensing circuits 810, 820, 830, 840, and 850, with exemplary model numbers and component values, are provided. The model number and component values are provided by way of example, and the circuits of Figured 8A-8E are in no way limited to the illustrated model numbers and component values, For instance, FIG. 8A illustrates a sensing circuit $10 that is implemented using a comparator transformer 812 coupled to a signal amplifier 814. A calibration offset adjust may be used, as well as an adjustable base-100 ohm resistor connected to the larger of two loads, which may be, for example, lamp arrays. In FIG. 8B, a comparator transformer of circuit 820 may be configured with resistors 822 and ground 824 connected to the current sensing loops.

Figure 8C:
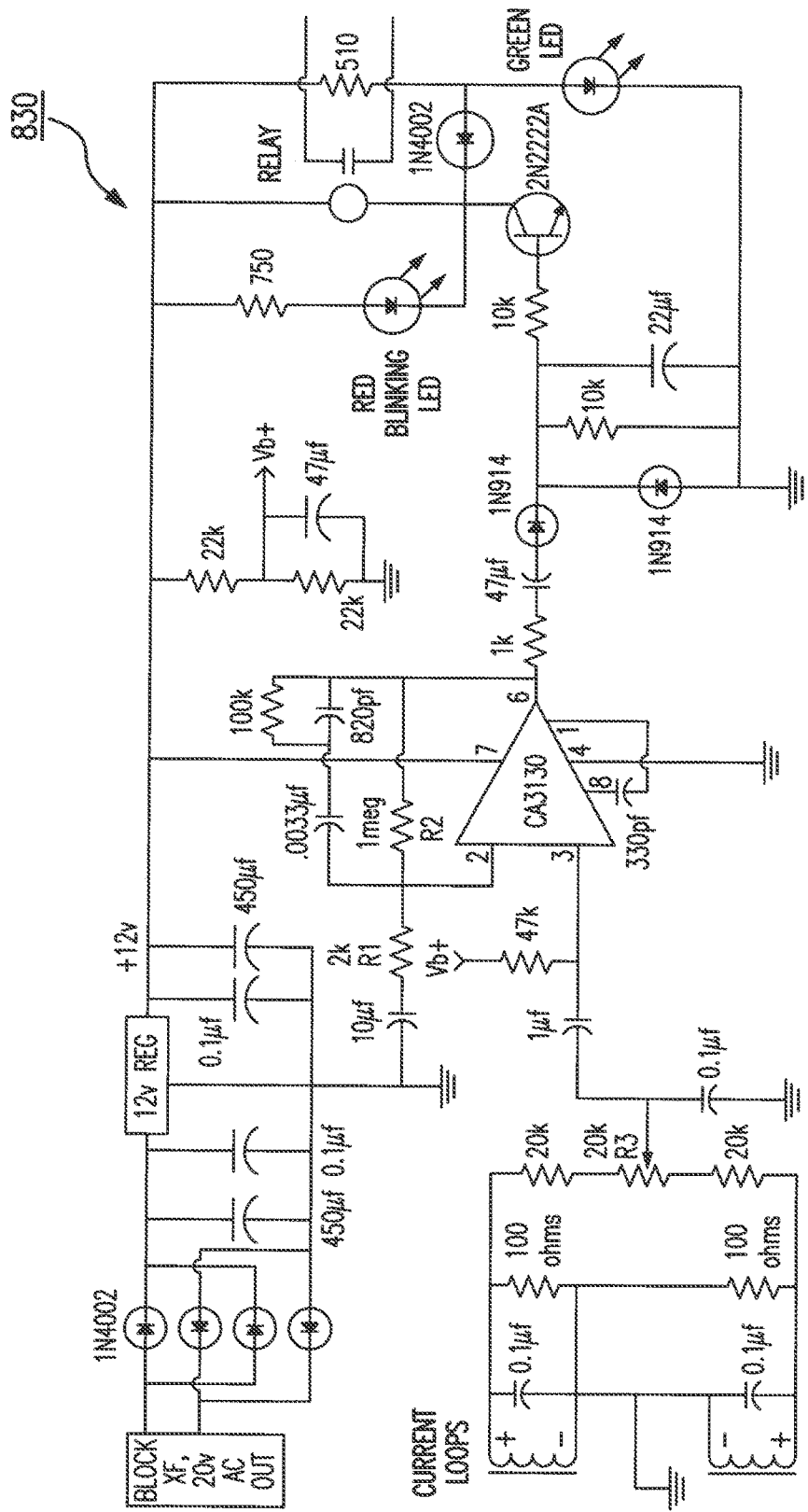
Figure 8D:
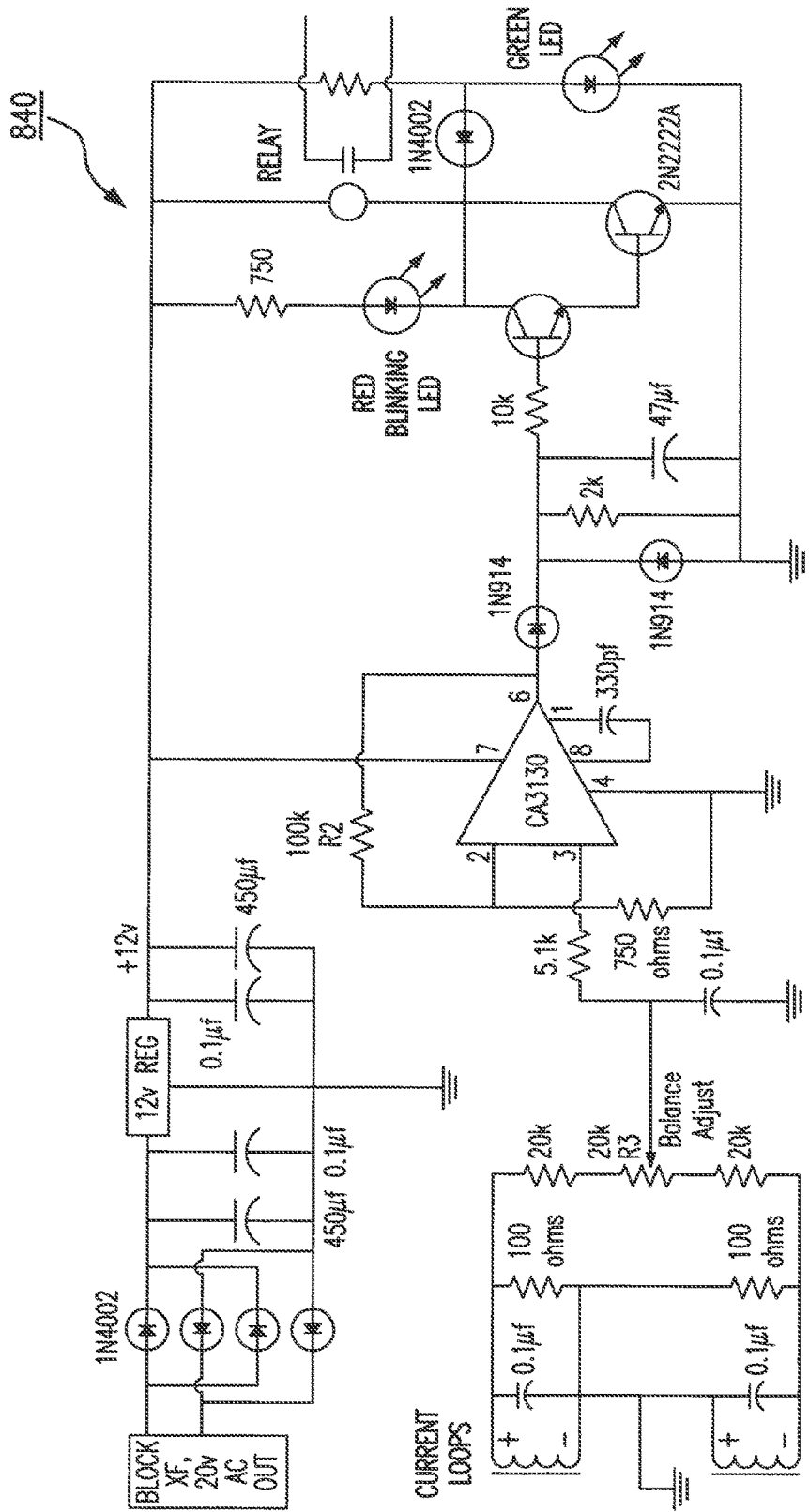
Figure 8E:
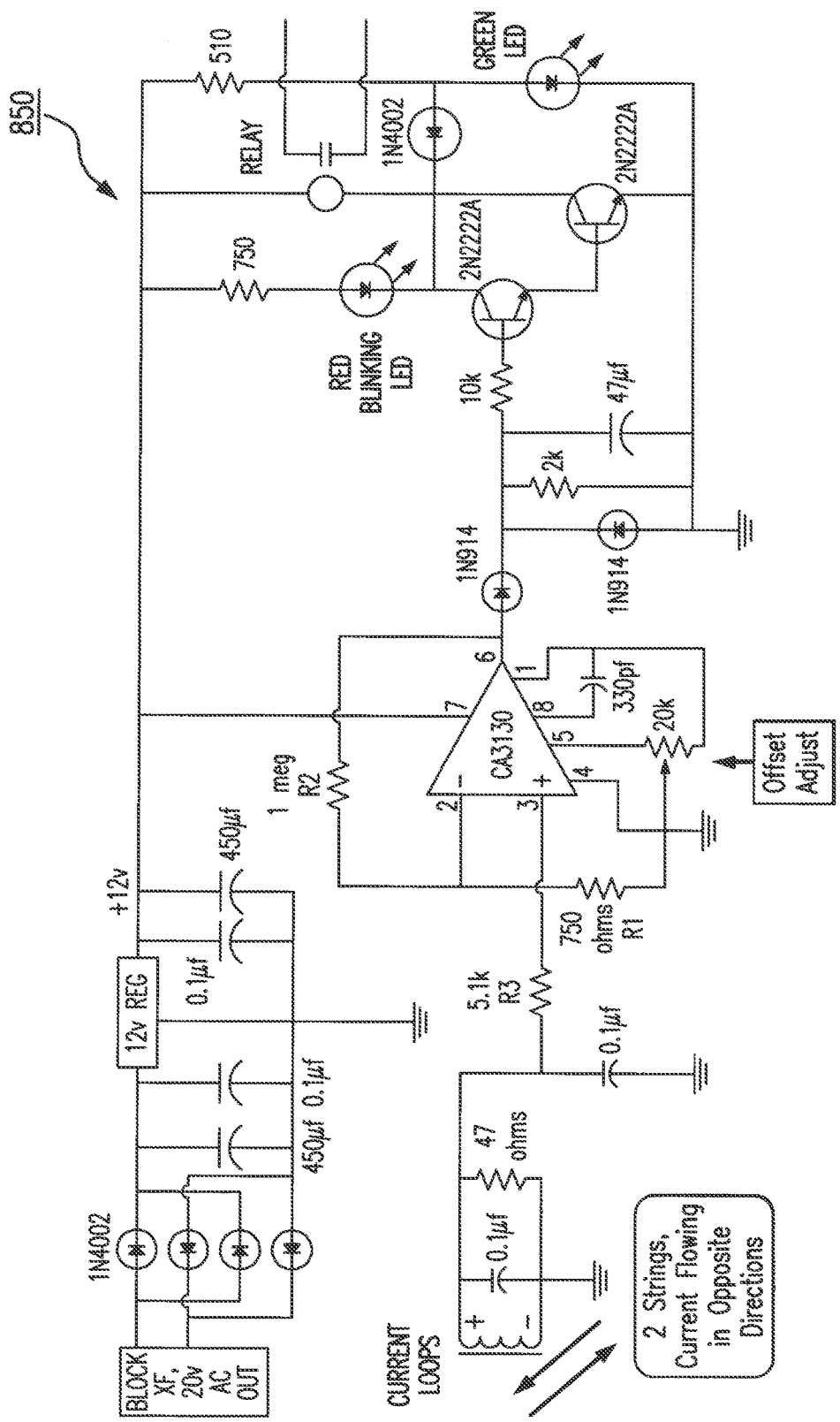

The exemplary sensing circuits 830,840 illustrated in FIGS. 8C and 8D are similar to sensing circuit 600, but do not include the amplifier-based power detection stage 608 shown in FIG. 6, In some embodiments, power detection and summing stages may not be required. The sensing circuitry 850 illustrated in FIG. 8E is similar to the configuration of FIG. 8D, but is based on sensing current through two strings, where the current is flowing in opposite directions, As is clear from the foregoing, one of ordinary skill in the art will recognize that the sensing, determining, and indicating means of the circuits disclosed herein can be implemented in numerous configurations and combinations.

Figure 9:
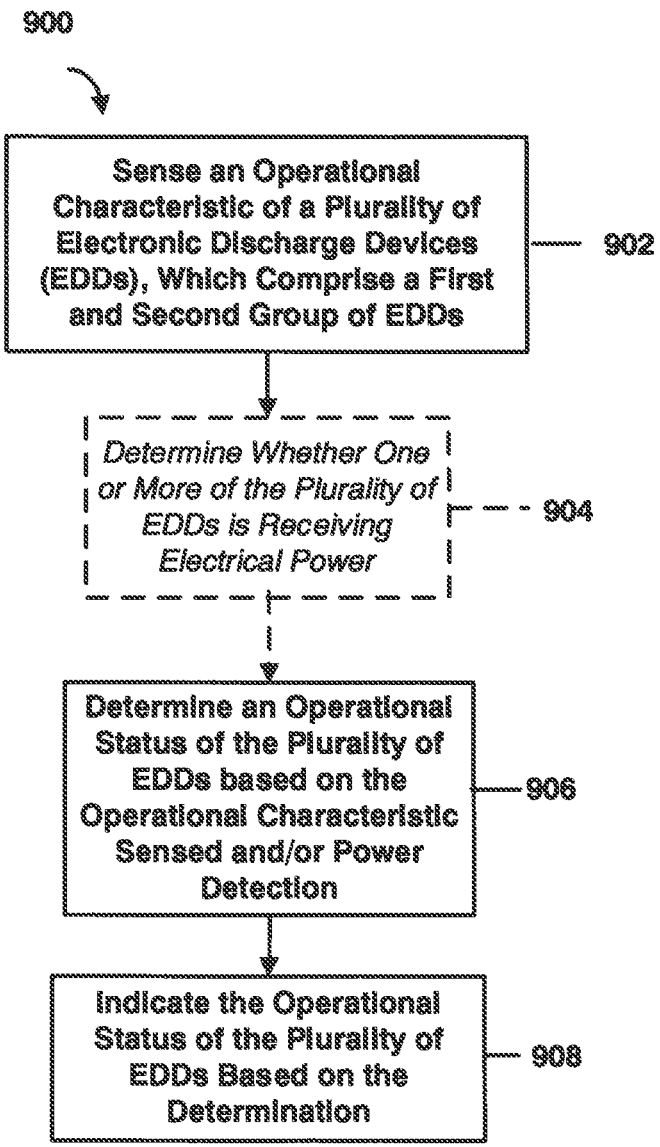
FIG. 9 is a flowchart of a method of monitoring the status of a plurality of electronic discharge devices in an air purification system according to an embodiment of the present invention

Referring now to FIG. 9, a process for remotely monitoring the operational status of a plurality of electronic discharge devices (EDDs) in an air purification system is provided, The process may include, for instance, monitoring the difference between an electrical property of a first and second group of EDDs in the plurality of EDDs. In some embodiments, the method may be performed by a sensing circuit, such as a sensing circuit as illustrated in FIGS. 6 and 8A-8E, In step 902, an operational characteristic of a plurality of EDDs is sensed, where the EDDs are separated into first and second groups. The EDDs may, for example, be part of an air purification system that has been installed or retrofitted to include electronics to sense electrical properties of the EDDs. For instance, the air purification system may include electronics to sense an imbalance in the current levels of two or more lamp arrays, where the lamp arrays have been grouped and setup as described in process 700 above.

In optional step 904, a determination is made as to whether one or more of the plurality of EDDs is receiving power. According to certain embodiments, if one or more EDDs is not receiving power, an alarm can be raised to an operator of the air purification system. For instance, an indication may be provided using the LEDs illustrated in FIG. 6.

In step 906, on operational status of the plurality of EDDs is determined. This determination may be based on the sensing performed in step 902. For instance, if there is a discrepancy between the electrical properties of the first and second group of EDDs, it may be determined that one or more EDDs is in need or service of has otherwise malfunctioned. In some embodiments, the determining of step 904 can include determining whether the difference in the relative current of a first and second group of electronic discharge devices exceeds a predetermined threshold. This threshold could be, for example, 10%. In certain aspects, if there is a power determination made, such as in step 904, the determination of step 906 may also be based on that determination, in addition to the sensing of step 902.

In step 908, the operational status of the plurality of EDDs is indicated, for instance, to the operator of the air purification system. This indication can be based on the determination of step 906 The indication can include, for example, illumination or extinguishing an, indicator light, such as the LEDs illustrated in FIG. 6. In some embodiments, the indicating may include transmitting a status signal that indicates the operational status of the plurality of EDDs. The transmission may be to a location that is remote from both the plurality of EDDs and any sensing circuitry.

While the invention has been particularly taught and described with reference to certain preferred embodiments, those versed in the art will appreciate that minor modifications in form and detail may be made without departing from the spirit and scope of the invention. For example, the sensing circuit may include a gate device with fewer or more inputs, multiple gate devices, or a DIP switch to tailor the number of sensor inputs. In an alternate embodiment, the sensing circuit may be configured to identify a specific lamp that is malfunctioning. Furthermore, while the mounting mechanism is shown as a resilient, semicircular clip, it will be appreciated that various other mounting mechanisms can be used, including but not limited to U shaped or C-shaped clips, clamps that extend partially or completely around the lamp, cable ties, bands that wrap around the lamp, or adhesives.

All of the foregoing changes, modifications and alterations should be considered within the scope of the present invention as set forth in the appended claims.

What is claimed is:

1. A method of retrofitting an air purification system having a plurality of electronic discharge devices, comprising:
   installing a first current sensing loop to a first array of said plurality of electronic discharge devices;
   installing a second current sensing loop to a second array of said plurality of electronic discharge devices;
   performing a balance adjustment on a sensing circuit connected to said first and second current sensing loops,
   wherein said balance adjustment includes modifying an adjustable component of said sensing circuit such that said sensing circuit indicates that one or more electrical properties of said first and second array are balanced.

2. The method of claim 1, further comprising:
   prior to performing said balance adjustment, powering on said first and second arrays.

3. The method of claim 1, wherein said balance adjustment includes modifying the value of an adjustable impedance of said sensing circuit.

4. The method of claim 1, further comprising:
   performing a balance readjustment,
   wherein said balance readjustment includes modifying the value of an adjustable impedance of said sensing circuit.

5. The method of claim 1, further comprising:
   identifying a balancing window.

6. An apparatus for remotely monitoring an operational status of a plurality of electronic discharge devices in an air purification system, comprising;
   a sensing stage having at least one adjustable impedance element and configured to measure a first electrical property of a first array of said plurality of electronic discharge devices and a second electrical property of a second array of said plurality of electronic discharge devices;

an imbalance detection stage configured to generate an operational status signal indicative of whether a difference between said first and second electrical properties exceeds a predetermined threshold; and an indicator, wherein said indicator is configured to provide an indication of said operational status based at least in part on said operational status signal.

7. The apparatus of claim 6, wherein, said first electrical property and said second electrical property are current and said sensing stage includes one or more current sensing loops.

8. The apparatus of claim 6, wherein said indicator includes one or more light emitting diodes (LEDs).

9. The apparatus of claim 6, wherein said indicator is configured to transmit an indication of said operational status to a location remote from said plurality of electronic discharge devices.

10. The apparatus of claim 6, further comprising:

a power detection stage configured to generate a power signal indicative of whether one or more of said plurality of electronic discharge devices is receiving electrical power, wherein said indicator is further configured to provide an indication of said operational status based at least hi part on said power signal.

* * * * *

UNITED STATES PATENT AND TRADEMARK OFFICE
CERTIFICATE OF CORRECTION

PATENT NO. : 9,792,804 B2
APPLICATION NO. : 15/452142
DATED : October 17, 2017
INVENTOR(S) : Zhang et al.

Page 1 of 1

It is certified that error appears in the above-identified patent and that said Letters Patent is hereby corrected as shown below:

In the Specification

In the Field of the Invention
Column 1, Line 19 change "systems, More" to --systems. More--.

Signed and Sealed this
First Day of May, 2018

Andrei Iancu
*Director of the United States Patent and Trademark Office*